United States Patent [19]
Castillo et al.

[11] Patent Number: 5,662,919
[45] Date of Patent: Sep. 2, 1997

[54] SULFATED POLYVINYL ALCOHOL POLYMERS TO STABILIZE PHARMACEUTICAL DRUG COMPOUNDS

[75] Inventors: Ernesto J. Castillo, Arlington; Yusuf Ali; Ruma P. Sarkar, both of Fort Worth, all of Tex.

[73] Assignee: Alcon Laboratories, Inc., Fort Worth, Tex.

[21] Appl. No.: 342,523

[22] Filed: Nov. 21, 1994

[51] Int. Cl.⁶ .............................. A61K 9/10; A61K 47/32
[52] U.S. Cl. ...................... 424/427; 424/460; 424/435
[58] Field of Search ........................ 424/427, 78.1, 424/78.11; 514/772.4

[56] References Cited

U.S. PATENT DOCUMENTS

| | | | |
|---|---|---|---|
| 3,987,163 | 10/1976 | Rankin | 424/78 |
| 4,465,666 | 8/1984 | Lukas et al. | 424/78.05 |
| 4,842,849 | 6/1989 | Grollier et al. | 424/70.15 |
| 4,911,920 | 3/1990 | Jani et al. | 424/78 |
| 4,971,079 | 11/1990 | Talapin et al. | 131/359 |
| 5,093,126 | 3/1992 | Jani et al. | 424/428 |
| 5,227,372 | 7/1993 | Folkman | 514/58 |

FOREIGN PATENT DOCUMENTS

| | | |
|---|---|---|
| 0 392 487 A2 | 10/1990 | European Pat. Off. . |
| 2-83318 | 3/1990 | Japan . |

*Primary Examiner*—Edward J. Webman
*Attorney, Agent, or Firm*—Patrick M. Ryan

[57] ABSTRACT

Stable formulations of positively charged, hydrolytically unstable drug compounds are obtained by adding a sulfated polyvinyl alcohol copolymer to the formulations.

26 Claims, No Drawings

SULFATED POLYVINYL ALCOHOL POLYMERS TO STABILIZE PHARMACEUTICAL DRUG COMPOUNDS

BACKGROUND OF THE INVENTION

1. Field of the Invention

The present invention relates to stable compositions of hydrolytically unstable pharmaceutical compounds. In particular, this invention relates to stable compositions containing positively charged, hydrolytically unstable drug compounds and sulfated polyvinyl alcohol polymers.

2. Description of Related Art

Epinephrine is an ophthalmic drug which has been Used for many years in the treatment of glaucoma. When topically administered to the eye, epinephrine can cause irritation, tearing, conjunctival hyperemia, and other side effects. The dipivalyl ester of epinephrine has been developed as a prodrug in an attempt to eliminate epinephrine's undesirable side effects. This epinephrine prodrug is known as dipivefrine hydrochloride or dipivalyl epinephrine ("DPE").

One of the problems associated with DPE in solution, however, is its instability due to ester hydrolysis and/or oxidation, causing a relatively short shelf-life.

One known method of improving the stability and/or comfort of certain pharmaceutical drug compounds is complexing the drug compound with certain ion-exchange resins. Such a method is disclosed in, for example, U.S. Pat. Nos. 4,911,920 and 5,093,126, where sustained release ophthalmic formulations of topical anti-glaucoma drugs include a water insoluble ion-exchange resin such as a sodium poly(styrenedivinyl benzene) sulfonate, to provide an additional means of sustained release and to improve comfort.

Ophthalmic solutions containing polystyrene sulfonate compounds are disclosed in U.S. Pat. No. 3,987,163. The reference solutions can be used to treat "dry eye" or as a carrier for ophthalmic medicaments. When used as a carrier, the reference solutions provide prolonged duration of medicament activity.

European Patent Application Publication No. 0 392 487 discloses a stabilized pharmaceutical composition containing an anthracycline antibiotic having an amino sugar residue and a certain kind of water-soluble polyanion capable of at least 40% interacting with the antibiotic. The water-soluble polyanions are natural and synthetic polymers having negatively charged acidic residues, such as sulfuric or sulfonic acid residues, and have a molecular weight of 500 to 2,000,000. Listed examples of natural polyanions include polysaccharides preferably having 1.5 to 3 sulfuric acid residues per repeating unit sugar. Dextransulfate is listed as one example of a natural macromolecular polyanion. The synthetic polymers include, among others, polystyrene and polyvinyl alcohol each preferably having 0.2 to 1.0 sulfuric acid residue per monomer unit. The reference anthracycline antibiotic composition possess improved stability in the neutral pH region.

SUMMARY OF THE INVENTION

The present invention provides stable compositions of positively charged, hydrolytically unstable drug compounds. The compositions of the present invention comprise one or more sulfated polyvinyl alcohol ("PVS") copolymers and one or more positively charged, hydrolytically unstable drug compounds.

The present invention also provides for a method of improving the stability of compositions containing positively charged, hydrolytically unstable ophthalmic drug compounds, wherein the method comprises adding one or more PVS copolymers to such compositions.

DETAILED DESCRIPTION OF THE INVENTION

The compositions of the present invention comprise one or more positively charged, hydrolytically unstable drug compounds and one or more PVS copolymers in an amount effective to stabilize such compound or compounds.

The PVS copolymers useful in the compositions and methods of the present invention are block or random copolymers having the formula

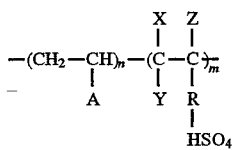

wherein n and m represent degrees of polymerization and n=5–2,500;

m=10–7,000;

A=H, OH, or $C_1$–$C_6$ alkyl;

X and Y independently=H or $CH_3$;

Z=H or $C_1$–$C_6$ alkyl; and

R=nothing, $C_1$–$C_6$ alkyl, or benzyl; provided that if Z=$C_1$–$C_6$ alkyl, R=nothing.

Suitable PVS copolymers will typically have a molecular weight from 2,000 to 1.2 million and a degree of sulfonation of at least 20%. Preferably, the PVS copolymers will have a molecular weight from 20,000 to 500,000, and most preferably from 100,000 to 300,000.

The preferred PVS copolymers are those of the formula listed above wherein, A=OH; X, Y and Z=H; and R=nothing or benzyl.

The most preferred PVS copolymers for use in the compositions of the present invention are those wherein A=OH; X, Y and Z=H; and R=nothing; such that they have the formula

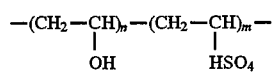

where n and m have the same values as those above. The degree of sulfonation of these most preferred PVS polymers is preferably at least 40% and is most preferably from 55 to 75%.

PVS may be prepared by sulfating polyvinyl alcohol, a commercially available polymer, using methods known in the art. Generally, PVS is synthesized by partially or completely hydrolyzing polyvinyl acetate to obtain a polyvinyl alcohol. The polyvinyl alcohol is then reacted with a sulfuric acid to obtain a PVS copolymer. Alternatively, certain PVS copolymers are commercially available as a sodium or potassium salt from Aldrich Chemical Company (Milwaukee, Wis.) and Eastman Kodak Company (Rochester, N.Y.).

The amount of PVS necessary to enhance the hydrolytic stability of the pharmaceutical compositions of the present invention will depend on a variety of factors, such as the type and amount of positively charged drug compound(s) to be stabilized and the target shelf-life or degree of stabilization desired. Typically, the amount of PVS contained in the compositions of the present invention will range from 0.05 to 5.0%. Preferably, the amount will range from 0.1 to 1.0. Most preferred are PVS concentrations ranging from 0.1 to 0.4%.

Suitable drug compounds useful in the compositions of the present invention include any positively charged drug compound capable of complexing with PVS and for which it is desirable to enhance hydrolytic stability. Examples of such positively charged drug compounds include DPE and prodrugs containing esters. DPE is especially preferred.

In addition to one or more PVS polymers and one or more positively charged drug compounds, the compositions of the present invention may optionally contain ingredients conventionally employed in pharmaceutical compositions. Examples of such other ingredients include, but are not limited to, preservatives, buffering agents, tonicity agents, chelating agents, viscosity enhancing agents, agents to adjust pH, antioxidants, ion-exchange resins and the like.

The composition of the present invention may be formulated for a variety of administration routes including, but not limited to, oral, parental, topical and nasal administration routes. Most preferred are compositions formulated for topical ophthalmic administration.

Certain embodiments of the present invention are illustrated in the following examples.

| Ingredient | % (w/v) |
|---|---|
| Example 1: Stable, Topical Ophthalmic Suspension | |
| DPE | 0.22% |
| PVS | 0.40% |
| benzalkonium chloride ("BAC") | 0.01% |
| Mannitol | 0.5% |
| Boric acid | 0.5% |
| Antioxidant | 0.16% |
| NaOH/HCl | QS pH 3.2 |
| Purified Water | QS 100% |
| Comparative Example 1: Ophthalmic Solution Without PVS | |
| DPE | 0.11 |
| BAC | 0.01 |
| EDTA | 0.0138 |
| NaCl | 0.88 |
| NaOH/HCl | QS pH 3.0 |
| Purified Water | QS 100% |
| Example 2: Stable, Topical Ophthalmic Suspension | |
| DPE | 0.11 |
| Betaxolol | 0.28 |
| Amberlite ® IRP-69 | 0.25 |
| PVS | 0.20 |
| Boric acid | 0.50 |
| Mannitol | 4.0 |
| Carbomer 974P | 0.3 |
| Lauroyl sarcosinate | 0.03 |
| EDTA | 0.01 |
| BAC | 0.011 |
| NaOH/HCl | pH: 5.5–5.8 |
| Purified Water | QS 100% |
| Comparative Example 2: Ophthalmic Suspension Without PVS | |
| DPE | 0.1 + 25% excess |
| Betaxolol | 0.28 |
| Amberlite ® IRP-69 | 0.25 |
| Boric Acid | 1.0 |
| Mannitol | 0.5 |
| Carbomer 974P | 0.35 |
| Lauroyl sarcosinate | 0.03 |
| EDTA | 0.01 |
| BAC | 0.01 |
| Sodium thiosulfate | 0.20 |
| NaOH/HCl | QS pH 7.0 |
| Purified Water | QS 100% |

| Ingredient | % (w/v) |
|---|---|
| Example 3: Stable, Topical Ophthalmic Suspension | |
| DPE | 0.11 |
| Betaxolol | 0.28 |
| PVS | 0.2 |
| Mannitol | 4.0 |
| EDTA | 0.01 |
| Lauroyl sarcosinate | 0.03 |
| BAC | 0.01 |
| Boric acid | 0.5 |
| NaOH/HCl | QS pH 4.5 |
| Purified Water | QS 100% |

The stability-enhancing effectiveness of the PVS polymers of the present invention was evaluated as follows. The formulations described in Examples 1–3 and Comparative Examples 1 and 2 above were placed in either plastic bottles or glass ampules and placed in controlled temperature ovens (room temperature, 35° C., 45° C., 55° C., and 65° C., 75° C., and 85° C.). Samples were pulled at predetermined times (1 day to 26 weeks). Arrhenius plots were obtained and shelf life was calculated by extrapolation at the desired temperature.

The results are shown in Table 1 below.

TABLE 1

| Formulation | Calculated Shelf-Life at RT (weeks) | Formulation | Calculated Shelf-Life at RT (weeks) |
|---|---|---|---|
| Example 1 pH = 3.2 | 465 | Comparative Example 1 pH = 3.2 | 81 |
| Example 2 pH = 5.8 | 132 | Comparative Example 2 pH = 7.0 | 8 |
| Example 3 pH = 4.5 | 125 | — | — |

As shown in the above table, the shelf-life of DPE is greatly enhanced by the use of PVS in the compositions. The stability enhancement of the formulation of Example 1 was approximately 500%, and the enhancement for the formulation of Example 2 was approximately 1600%.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed:

1. A hydrolytically stable, aqueous pharmaceutical composition having a pH of about 3.2 or greater comprising a therapeutically-effective amount of a positively charged, hydrolytically unstable drug compound and a sulfated polyvinyl alcohol block or random copolymer in an amount effective to hydrolytically stabilize the drug, wherein the sulfated polyvinyl alcohol copolymer has the formula

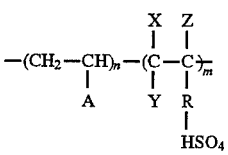

wherein n and m represent degrees of polymerization and n=5–2,500;

m=10–7,000;

A=OH;

X and Y independently=H or CH$_3$;

Z=H or C$_1$–C$_6$ alkyl; and

R=nothing, C$_1$–C$_6$ alkyl, or benzyl; provided that if Z=C$_1$–C$_6$ alkyl, R=nothing;

provided that the drug compound is not an anthracycline antibiotic having an amino sugar residue, and further provided that the composition does not contain an antiviral amount of zinc ions.

2. The composition of claim 1 wherein X, Y and Z=H; and R=nothing or benzyl.

3. The composition of claim 2 wherein R=nothing.

4. The composition of claim 1 wherein the sulfated polyvinyl alcohol copolymer has a molecular weight from 2,000–1.2 million.

5. The composition of claim 4 wherein the sulfated polyvinyl alcohol copolymer has a molecular weight from 20,000–500,000.

6. The composition of claim 5 wherein the sulfated polyvinyl alcohol copolymer has a molecular weight from 100,000–300,000.

7. The composition of claim 1 wherein the sulfated polyvinyl alcohol copolymer has a degree of sulfation of at least 20%.

8. The composition of claim 3 wherein the sulfated polyvinyl alcohol copolymer has a degree of sulfation of at least 40%.

9. The composition of claim 8 wherein the degree of sulfation is from 55–75%.

10. The composition of claim 1 wherein the amount of sulfated polyvinyl alcohol copolymer is from 0.05 to 5% (w/v).

11. The composition of claim 10 wherein the amount of sulfated polyvinyl alcohol copolymer is from 0.1 to (w/v).

12. The composition of claim 11 wherein the amount of sulfated polyvinyl alcohol copolymer is from 0.1 to 0.4% (w/v).

13. The composition of claim 1 wherein the drug compound is dipivalyl epinephrine and the composition is a topically administrable ophthalmic composition.

14. A method of improving the stability of an aqueous composition containing a therapeutically-effective amount of a positively charged, hydrolytically unstable drug compound and having a pH of about 3.2 or greater, wherein the method comprises adding to the composition a hydrolytically stabilizing amount of a sulfated polyvinyl alcohol copolymer of the formula

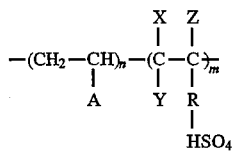

wherein n and m represent degrees of polymerization and n=5–2,500;

m=10–7,000;

A=OH;

X and Y independently=H or CH$_3$;

Z=H or C$_1$–C$_6$ alkyl; and

R=nothing, C$_1$–C$_6$ alkyl, or benzyl; provided that if Z=C$_1$–C$_6$ alkyl, R=nothing;

and provided that the drug compound is not an anthracycline antibiotic having an amino sugar residue.

15. The method of claim 14 wherein X, Y and Z=H; and R=nothing or benzyl.

16. The method of claim 15 wherein R=nothing.

17. The method of claim 14 wherein the sulfated polyvinyl alcohol coploymer has a molecular weight from 2,000–1.2 million.

18. The method of claim 17 wherein the sulfated polyvinyl alcohol copolymer has a molecular weight from 20,000–500,000.

19. The method of claim 18 wherein the sulfated polyvinyl alcohol copolymer has a molecular weight from 100,000–300,000.

20. The method of claim 14 wherein the sulfated polyvinyl alcohol copolymer has a degree of sulfation of at least 20%.

21. The method of claim 16 wherein the sulfated polyvinyl alcohol copolymer has a degree of sulfation of at least 40%.

22. The method of claim 21 wherein the degree of sulfation is from 55–75%.

23. The method of claim 14 wherein the amount of sulfated polyvinyl alcohol copolymer is from 0.05 to 5% (w/v).

24. The method of claim 23 wherein the amount of sulfated polyvinyl alcohol copolymer is from 0.1 to 1 (w/v).

25. The method of claim 24 wherein the amount of sulfated polyvinyl alcohol copolymer is from 0.1 to 0.4% (w/v).

26. The method of claim 14 wherein the drug compound is dipivalyl epinephrine and the composition is a topically administrable ophthalmic composition.

* * * * *